(12) United States Patent
Webster et al.

(10) Patent No.: US 9,377,407 B2
(45) Date of Patent: Jun. 28, 2016

(54) REACTION MONITORING

(75) Inventors: Benjamin Masterman Webster, Cleveland (GB); James Richard Howell, Middlesbrough (GB)

(73) Assignee: IT-IS International Limited (GB)

( * ) Notice: Subject to any disclaimer, the term of this patent is extended or adjusted under 35 U.S.C. 154(b) by 978 days.

(21) Appl. No.: 12/297,261

(22) PCT Filed: Apr. 18, 2007

(86) PCT No.: PCT/GB2007/001415
§ 371 (c)(1),
(2), (4) Date: Jun. 1, 2009

(87) PCT Pub. No.: WO2007/119067
PCT Pub. Date: Oct. 25, 2007

(65) Prior Publication Data
US 2010/0015611 A1     Jan. 21, 2010

Related U.S. Application Data

(60) Provisional application No. 60/745,163, filed on Apr. 19, 2006.

(51) Int. Cl.
*C12Q 1/68* (2006.01)
*G01N 21/64* (2006.01)

(52) U.S. Cl.
CPC ........ *G01N 21/6428* (2013.01); *G01N 21/6452* (2013.01); *G01N 21/6456* (2013.01); *G01N 2021/6421* (2013.01); *G01N 2021/6441* (2013.01)

(58) Field of Classification Search
CPC .......... G01N 21/6428; G01N 21/6454; G01N 2021/6421; G01N 2021/6441; G01N 21/6452; G01N 21/6456

See application file for complete search history.

(56) References Cited

U.S. PATENT DOCUMENTS

| | | | |
|---|---|---|---|
| 4,484,817 A | 11/1984 | Nobuto et al. | |
| 5,952,202 A * | 9/1999 | Aoyagi et al. | 435/91.2 |
| 7,897,337 B2 * | 3/2011 | Macioszek et al. | 435/6.11 |
| 2003/0012693 A1 | 1/2003 | Otillar et al. | |
| 2003/0048493 A1 | 3/2003 | Pontifex et al. | |
| 2003/0175987 A1 | 9/2003 | Verdonk et al. | |
| 2004/0191758 A1 | 9/2004 | Bearman et al. | |
| 2004/0225222 A1 | 11/2004 | Zeng et al. | |
| 2005/0088653 A1 | 4/2005 | Coates et al. | |
| 2005/0133724 A1 * | 6/2005 | Hsieh et al. | 250/339.12 |
| 2006/0051878 A1 | 3/2006 | Dickson et al. | |

* cited by examiner

*Primary Examiner* — Young J Kim
(74) *Attorney, Agent, or Firm* — Hartman Global IP Law; Gary M. Hartman; Michael D. Winter

(57) ABSTRACT

The invention provides a method and apparatus for detecting a signal of a specific spectrum emitted in the course of a chemical or biochemical reaction. The method comprises conducting the reaction in a reaction vessel, which is arranged so that light emanating from the reaction vessel is received by a detector comprising a plurality of photosensors in an array, wherein each photosensor is activated by light falling within a particular waveband range only, and where photosensors activated by light in different waveband ranges are distributed throughout the array. Output from one or more subsets of those photosensors which receive wavebands which contribute to the said specific spectrum is monitored and the output from a subset, or the relationship between the outputs of each subset are used to determine the signal in the specific spectrum.

10 Claims, 6 Drawing Sheets

| R | G | R | G | R | G | R | G |
|---|---|---|---|---|---|---|---|
| G | B | G | B | G | B | G | B |
| R | G | R | G | R | G | R | G |
| G | B | G | B | G | B | G | B |
| R | G | R | G | R | G | R | G |
| G | B | G | B | G | B | G | B |

Figure 2

VIC Calc. Levels with Varying FAM

| FAM | VIC 0.0 | VIC 0.5 | VIC 1.0 |
|---|---|---|---|
| 0 | -0.002 | 0.501 | 1.001 |
| 0.1 | -0.009 | 0.506 | 1.007 |
| 0.2 | 0.01 | 0.493 | 1.008 |
| 0.3 | 0.002 | 0.501 | 1 |
| 0.4 | 0 | 0.492 | 0.994 |
| 0.5 | 0.008 | 0.497 | 1 |
| 0.6 | 0.002 | 0.519 | 1 |
| 0.7 | -0.006 | 0.501 | 0.99 |
| 0.8 | 0 | 0.493 | 0.998 |
| 0.9 | -0.003 | 0.496 | 1.002 |
| 1 | 0.005 | 0.494 | 1 |

REACTION MONITORING

CROSS-REFERENCES TO RELATED APPLICATIONS

This application is a U.S. National Stage Application of PCT/GB2007/001415, filed Apr. 18, 2007, which claims priority from U.S. Provisional Patent Application No. 60/745,163, filed Apr. 19, 2006, each of which are incorporated herein by reference.

The present invention relates to a method for detecting signals in particular, though not exclusively, visible signals having particular spectra emanating from reaction vessels in which chemical or biochemical reactions are carried out, as well as apparatus for use in these methods.

Many chemical and biochemical reactions are carried out using reagents which produce a detectable signal in particular a visible signal, such as a fluorescent, chemiluminescent or bioluminescent signal, which occur or are modified under certain reaction conditions.

Detection of these signals may be used in a variety of ways. In particular they can allow for the detection of the occurrence of a reaction, which may be indicative of the presence or absence of a particular reagent in a test sample, or to provide information about the progress or kinetics of a particular reaction.

As these types of reagents are used more widely, the way they are used becomes more and more complex. In many instances a reaction mixture may contain more than one such "signaling" reagent, and the signals from these may need to be detected or monitored over time, in order to provide a full set of information about the occurrence, nature or progress of a particular reaction.

A particular example of a reaction where detectable signals and in particular fluorescent signals are monitored is in nucleic acid amplification techniques and in particular the polymerase chain reaction (PCR). Amplification of DNA by polymerase chain reaction (PCR) is a technique fundamental to molecular biology. PCR is a widely used and effective technique for detecting the presence of specific nucleic acids within a sample, even where the relative amounts of the target nucleic acid is low. Thus it is useful in a wide variety of fields, including diagnostics and detection as well as in research.

Nucleic acid analysis by PCR requires sample preparation, amplification, and product analysis. Although these steps are usually performed sequentially, amplification and analysis can occur simultaneously.

In the course of the PCR, a specific target nucleic acid is amplified by a series of reiterations of a cycle of steps in which nucleic acids present in the reaction mixture are denatured at relatively high temperatures, for example at 95° C. (denaturation), then the reaction mixture is cooled to a temperature at which short oligonucleotide primers bind to the single stranded target nucleic acid, for example at 55° C. (annealing). Thereafter, the primers are extended using a polymerase enzyme, for example at 72° C. (extension), so that the original nucleic acid sequence has been replicated. Repeated cycles of denaturation, annealing and extension result in the exponential increase in the amount of target nucleic acid present in the sample.

DNA dyes or fluorescent probes can be added to the PCR mixture before amplification and used to analyse the progress of the PCR during amplification. These kinetic measurements allow for the possibility that the amount of nucleic acid present in the original sample can be quantitated.

Monitoring fluorescence each cycle of PCR initially involved the use of a fluorophore in the form of an intercalating dye such as ethidium bromide, whose fluorescence changed when intercalated within a double stranded nucleic acid molecule, as compared to when it is free in solution. These dyes can also be used to create melting point curves, as monitoring the fluorescent signal they produce as a double stranded nucleic acid is heated up to the point at which it denatures, allows the melt temperature to be determined.

By monitoring the change in fluorescence from the dye as the PCR progresses (and it will progress only if at least some target nucleic acid is present in the sample initially) the bulk change in the amount of nucleic acid present in the reaction mixture can be monitored. This type of system is described for example in EP-A-512334. In this system, fluorescence is measured once per cycle as a relative measure of product concentration. Furthermore, the cycle number where an increase in fluorescence is first detected increases inversely proportionally to the log of the initial template concentration.

Other fluorescent systems have been developed that are capable of providing additional data concerning the nucleic acid concentration and sequence. In many of these systems, fluorescently labeled probes, which are oligonucleotides which hybridise specifically to the amplified sequence, are included instead of or in addition to the intercalating dye.

Particular examples of such as system are available commercially as the "Taqman"™ system, but there are many others including some specific examples as set out in WO/9746707A2, WO/9746712A2, WO/976714A1, all published Dec. 11, 1997, the entire content of which are incorporated herein by reference.

In these more complex systems, more than one fluorophore, generally in the form of fluorescent labels, are incorporated into the reaction system. For example, in the Taqman™ system, a probe carrying two fluorescent labels is added to the system. The fluorescent signal from the labels is interactive using fluorescence energy transfer (FET), a particular type of which is fluorescence resonant energy transfer (FRET), so that light emitted from one label (the energy donor or reporter) is absorbed by the other label (the energy acceptor or quencher) when these two are in close proximity to each other on the probe. The probes are designed to be annealed to the amplified or target sequence during the extension phase of each cycle of the PCR. The polymerase enzyme utilized in this reaction is one which has a 5'-3'exonuclease activity, and therefore, when the probe is encountered during the extension, it is digested by the enzyme. This digestion results in separation of the two labels, meaning that FET or FRET can no longer occur, and the resultant signals from the labels changes as a result.

In these systems, sample analysis occurs concurrently with amplification in the same tube within the same instrument. This combined approach decreases sample handling, saves time, and greatly reduces the risk of product contamination for subsequent reactions, as there is no need to remove the samples from their closed containers for further analysis. The concept of combining amplification with product analysis has become known as "real time" PCR.

However, the fact that these systems produce complex and often overlapping signals, from multiple different fluorophores within the system means that complex signal resolution is required to determine the intensity of the signal from the individual fluorophores.

The complexity is further compounded in that PCRs are generally conducted in specifically constructed thermal cyclers, such as block heaters, which accommodate multiple reaction vessels at the same time. These are then cycled together, and the signals produced by each vessel monitored.

Current systems for PCR fluorimetry often rely on detection systems such as monochrome detectors (CCD, photodiode, PMT, CMOS detectors etc.) which on their own will only detect the presence or absence of light, but cannot distinguish amongst light of different wavebands or colours. Therefore they are not able directly to differentiate between the various different fluorophore signals. This problem is often addressed by having an external means of separating or filtering light into different wavebands for detection at different points on the detector, or at different points in time.

These external means increase the cost, size and complexity of the instrument. Such external means often need to be precisely mounted for optical alignment, and this tends to reduce the robustness of the instrument or leads to increased size, weight and cost associated with the mounting.

Specifically, such external means include moving filter sets, where multiple filters are combined in such a way that a physical actuator may position one of the filters in front of the monochrome detector, allowing for detection of a particular waveband.

Other systems use a fixed filter set or diffraction grating to produce separate wavebands, but in this case the wavebands are spatially separated on the detector, and this removes the ability of the sensor simultaneously to detect emissions from an entire two-dimensional arrangement of vessels. This leads to the need for a scanning or other moving system to direct emissions from different vessels to the detector, or to move the vessels into alignment with the detector.

In each of these systems, in order to detect different wavebands or vessel emissions, the actuator(s) must move to a new position for each reading, incurring a time delay between each reading, and also dividing the acquisition time for each waveband by the number of wavebands acquired, or where the actuator must move to acquire from different vessels or vessels, dividing the acquisition time by the number of vessels or groups of vessels.

Many useful applications of PCR analysis rely on readings from multiple wavebands, and all require each vessel used to be measured, making this time delay inevitable. This has the effect of reducing the maximum rate of acquisitions, and hence reducing time resolution of measurements, which can be critical when the acquisitions are taken during a process such as a temperature ramp for the purposes of melt analysis.

In addition, since the readings for different wavebands or vessels are inevitably taken at different times, they are less useful for purposes of removing crosstalk between channels, noise from illumination, and other time dependent effects, and there will often be a temperature difference in the reactions between readings, which can affect analysis. Additionally, the detector cannot be used while any part is in motion, reducing the proportion of the time for which the detector can be acquiring, reducing integration time and sensitivity accordingly. Often, to mitigate these restrictions, PCR analysis is performed using only a subset of available wavebands, to reduce the number of filter movements required and so increase acquisition rate, but this means that potentially useful data is not acquired, and cannot be used for later analysis. The physical aspect of such moving systems also presents problems, since moving systems are inherently subject to wear over time, and are harder to seal, potentially increasing the accumulation of debris on the filter set and other degradation over time, reducing optical performance.

Where an instrument includes a moving filter set, or other moving parts, or separate detectors for different wavebands, such accuracy of alignment between acquisitions for different wavebands is difficult to achieve, and this both complicates the correction process and reduces the accuracy of the correction.

Detectors with integrated filters are widely available. In fact, they form the basis of many colour digital still and video cameras. In these detectors or "camera chips", arrays of photosensors are provided, and a colour filter is placed over each individual photosensor. By arranging different colour filters over adjacent photosensors in a precise pattern, it is possible to obtain enough information about the colour of the light in the general vicinity of each sensor to arrive at a true colour for the location. This process of averaging the signal from neighbouring photosensors is called interpolation. By interrogating the outputs in a different way however, in particular by combining only those signals from photosensors which receive one individual colour, images in a single spectrum, for example a green, blue or red spectrum, can be obtained.

Such devices have not been widely utilized previously in the detection of signals such as fluorescent signals from chemical or biochemical reactions, because they are not, in normal operating mode, considered to be sensitive enough to detect changes in these signals. Previous attempts to address this problem have focused on enhancing or modifying the signals generated to make them more readily detectable using a conventional CCD.

The applicants have found however that this technology can be applied to provide an effective and efficient method for detecting or monitoring chemical or biochemical reactions such as PCR.

According to a first aspect of the present invention there is provided a method for detecting a signal having a specific spectrum emitted in the course of a chemical or biochemical reaction, said method comprising conducting said reaction in a reaction vessel, which is arranged so that light emanating from the reaction vessel is received by a detector comprising a plurality of photosensors in an array, wherein each photosensor is activated by light falling within a particular waveband range only, and where photosensors activated by light in different waveband ranges are distributed throughout the array, and monitoring output from one or more subsets of those photosensors which receive wavebands which contribute to the said specific spectrum, and utilizing the output from a subset, and/or the relationship between outputs of more than one subset to determine the signal having that spectrum.

As used herein, the expression "reaction vessel" refers to any form of support or container in which the reaction may be carried out. Thus, it includes reaction tubes, wells in reaction plates as well as slides or chips.

Generally, the specific spectrum will be characteristic of a particular reagent such as a dye which is present in the chemical or biochemical reaction, and so the presence or absence, or intensity of the signal having that characteristic spectrum may be indicative of a property or state of the reaction mixture.

As used herein, the term "subset" refers to some but not all of the photosensors within the array. A "subset" will include all or most of the photosensors within the array that receive radiation, in particular light radiation, in one particular waveband range or colour spectrum, although a few may be used for control or calibration purposes. Effectively, in this way, by utilizing a single subset, one may obtain an image in a single colour spectrum. Individually, or in particular combinations, this can then be related to the level or intensity of output of the signal, which in general is derived from a specific reagent, such as a dye present in the chemical or biochemical reaction, which emits radiation in the specific waveband range.

The output from more than one subset of photosensors may be used to determine the signal having a particular spectrum. In particular the level of the signal in each wavelength range (or sub-spectrum) can be used as an indicator of the level of the signal having a specific spectrum, characteristic of a particular reagent such as a dye. Integration of the outputs in the same waveband range (corresponding effectively to colour type) across the entire vessel area provides a sensitive way of determining the actual signal in that waveband range.

By comparing the levels in more than one waveband range, and in particular in each individual waveband range (sub-spectrum), the signal to noise ratio is enhanced sufficiently to allow the sorts of signals that are emitted during chemical and biochemical reactions to be monitored.

The waveband ranges of the individual subsets are suitably selected so as to ensure that a signal having a specific spectrum which is to be detected falls predominantly within one subset. Alternatively, reagents used in the reaction which give rise to the signal may be selected so that they emit predominantly in the waveband range of a single subset of photosensors in a detector.

The determination process suitably is carried out using the raw data obtained from individual subsets of photosensors. By adjusting the sensor setting (gain/exposure), readings which are sensitive enough to detect changes in signal from say a particular dye, are detectable. Alternatively, where the outputs have been combined in a conventional operating mode, it is necessary to resolve those signals using a computer before the determination can be made.

One or more signals of specific spectrum are then determined either by utilizing the output from a single subset, or, more usually, the relationship between outputs of more than one subset to determine the signal having that spectrum, as outlined in more detail below.

As used herein, the expression "chemical or biochemical reaction" includes various operations in which reagents may react together in order to produce new or different reagents or products, and also the treatment of samples to determine the changes which take place in reagents under changing conditions, such as temperature, electrochemical potential or time. Thus the expression includes operations such as melting point analysis of reagents, as well as reactions such as the PCR.

The use of an array detector with photosensors sensitive to different wavelength bands or sub-spectra, provides for a substantial improvement on existing systems. The applicants have found, surprisingly, that the sensitivity of these systems is sufficient to distinguish dye signals such as fluorescent dye signals which may be emitted in the course of a chemical or biochemical reaction.

The detectors utilized in the method of the invention suitably comprise conventional array detectors such as charge coupled devices (CCDs), complementary metal oxide semiconductor devices (CMOSs), photodiodes or PMT devices, but are preferably CCDs.

In order to ensure that the individual photosensors within the arrays present in these devices are activated only by light within a certain waveband range or sub-spectrum, various methods can be used including the use of filter wheels or diffraction gratings, to ensure that light of specific waveband ranges reaches individual photosensors at any particular time. Other optical devices such as galvanic scanners can be used, for example to allow excitation light to be directed onto vessels one at a time, or for light to be directed through different filters in a sequence, or for light from different excitation sources to be utilized.

Of course, all photosensors will have their own particular inherent spectral sensitivity, and it may be the case that different photosensors can be chosen having different particular inherent spectral sensitivities. However in a particularly preferred embodiment, the detector is provided with an array of photosensors having similar inherent spectral sensitivities and a set of differently coloured optical filters. The set of differently coloured optical filters are provided between said reaction vessel and said photosensors, in fixed relation to the photosensors, so that light falling within a particular waveband range only activates each individual photosensor. The differently coloured optical filters are suitably arranged in a pattern, such that adjacent photosensors or groups of photosensors receive light of different waveband ranges. It will be apparent that at least one photosensor for each colour may be used as a control to enable accurate measurements of the spectral sensitivity to light of different wavelengths to be made for calibration. This would be especially useful if photosensors having different spectral sensitivities are used for different waveband ranges, so that their respective sensitivities to light of the same wavelength can be compared and taken into consideration. For example, this can be used to correct for not only sensor properties, but also for the properties of readout electronics, etc. and could also be used for correcting for changes in filter properties. Variations in sensor and readout electronics properties over temperature and lifetime of the device can also be compensated for.

This type of arrangement is used in many detectors such as CCDs which have integrated optical filters, which are fixed in very close proximity to the photosensors. They are precisely aligned at the individual photosensor level so that each photosensor receives light which passes through one colour filter only. The fixed integration of these filters into the device prevents misalignment and avoids the need for costly external filters or other filtering or waveband separating devices, and mounting arrangements for these.

Various arrangements of optical filters are known. The most commonly used arrangement is the Bayer filter or Bayer mask, which is described U.S. Pat. No. 3,971,065, the entire content of which is incorporated herein by reference.

In that arrangement, a picture element comprises a block of four different photosensors, one being provided with a fixed red filter, one being provided with a fixed blue filter, and the other two being provided with a fixed green filter. The arrangement of the colours within the Bayer mask is illustrated hereinafter in FIG. 2.

In a particular embodiment, all filters of one colour are provided on a single filter sheet in an appropriate arrangement, which is transparent in the areas where other filter colours are required. In this way, it is possible to construct an entire colour mask, with each photosensor correctly filtered with a limited number of filter sheets. The number of sheets can be reduced by including more than one appropriately arranged colour on each sheet. A single sheet on which all the colours are printed in an appropriate pattern may also be utilized. The block of four (one of which is illustrated in FIG. 2 by means of a thick line) will be referred to herein as a "pixel", and the individual photosensors are referred to herein as "sub-pixels". In practice, when the detector is utilized, the photosensors are progressive scanned, generally serially in rows. Scanning takes place almost instantaneously, and may, in some cases, be within a fraction of a second. The intensity of light received by each sub-pixel is measured.

In normal use, the outputs from each sub-pixel within a pixel are combined at this time to produce a point image which approximates in colour with the incident light.

In accordance with one embodiment of the invention however, a selection of the outputs from only those sub-pixels which are of a colour which corresponds to that of the target signal within the chemical or biochemical reaction is selected at this stage. Thus for example, when monitoring the signal emitted from a fluorescent dye such as SYBR Green I, it may be necessary to select output from only the sub-pixels which are activated by green light, and therefore in the case of the Bayer filter, one can average two signals to obtain a reading of the intensity of the light in the green spectrum at the point corresponding to the pixel. Similarly, by selecting only the output from the sub-pixel provided with a red filter, it is possible to detect the intensity of signal emitted by a red dye such as ethidium bromide, or by selecting only the output from the sub-pixel provided with a blue filter, it is possible to detect the intensity of signal emitted by a blue dye.

By selecting outputs in this way across the array, it is possible to generate an image of the reaction vessel in a single spectrum. Although there is a slight loss in spatial precision, in particular if a single sub-pixel type is selected, as the position of pixel in the single spectrum image will be that of the sub-pixel rather than the average of the pixel, this is insignificant in terms of the size of the reaction vessel. However, this selection allows any changes in say the intensity of the emission from a particular dye to be readily detected, and thus where this is indicative of the progress of a chemical or biochemical reaction, that can be assessed.

Most dyes will emit to some extent in all wavebands, but at different relative intensities, and so it may be convenient in some cases, to select more than one type of sub-pixel output, for example outputs from both red and green sub-pixels, or even from all of the red, green and blue sub-pixels independently, in order to arrive at an accurate signal intensity value. However, this will be dependent upon the nature of the signal being monitored, which will in general be determined by the properties of the particular dye used, and can be selected accordingly.

Where there is more than one dye within the chemical or biochemical reaction, provided these emit within different waveband ranges, it is possible to monitor each of them at the same time, by selecting outputs from photosensors which are provided with appropriate filters. For instance, when using a Bayer filter, one could detect signals from a red, a green and a blue dye simultaneously, by reading outputs from individual sub-pixel types.

As indicated above however, since most dyes will emit to some extent in all wavebands, it may be necessary to resolve the signal (level of each waveband) into levels of each dye by a calculation based on knowledge of the expected spectra of each dye. This type of deconvolution operation is conventional in the art, and will be readily apparent to a skilled person. In practice this is usually done via a matrix transform calculated from readings of known levels of dye in a calibration, possibly with readings taken at a range of different conditions, for example temperature. Where each dye emits at different relative intensities in each waveband range, it is generally possible to distinguish as many dyes as there are types of subpixels.

For example, where an essentially "red" dye X is used, it might emit for example 90% of its light in the red waveband, and 10% in the green waveband. A "green" dye Y might emit 10% red and 90% green. The output from the red subpixels alone will not be sufficient to determine the level of dye X, since in the presence of a large Y signal, X would be overestimated. If there is say 10 times as much Y as X, then this (dye Y) will actually generate as much red signal as from the "red" dye X.

However, since it is known that X always emits in this 9:1 ratio, and Y in a 1:9 ratio, it is possible still to accurately work out the level of each dye by reading both red and green, and using BOTH values in a calculation that yields BOTH dye levels, completely accounting for the dyes spilling over into each others colours:

$$R=0.9X+0.1Y$$

$$G=0.1X+0.9Y$$

$$=>$$

$$X=(9R-G)/8$$

$$Y=(9G-R)/8$$

This is an example where the relationship between the outputs of the green and red subsets are used to determine the signal.

From this can be seen that with any level of red and green readings for a vessel from the CCD, we can get back an exact X and Y dye level, even though both red and green are a mixture of readings from both dyes.

The number of dyes which can be easily read in this way is, by and large, limited to the number of colours types or subsets of photosensors (which will equate to the number of "channels" on a conventional CCD). It is necessary only that each dye emits predominantly in the waveband range detected by a different subset of photosensors.

Thus, where there is a blue channel, we could read an extra dye, using 3 equations instead of two. When the deconvolution is actually implemented, a matrix is used to get the levels of all dyes at once, rather than using equations as shown above, but the technique is mathematically identical. The "calibration" required to do this is essentially the process of actually working out that dye X emits 90% red and 10% green, and Y 10% red, 90% green, by just reading each dye on its own in a vessel.

In some cases, as a dye is heated, the ratio of say the red:green emission may change, and therefore, it is preferable to calibrate the deconvolution process at the temperature at which the reaction or the reaction stage at which the signal is measured, is going to be carried out.

As discussed above, selection of output is preferably done on the basis of the direct output from the individual photosensors or sub-pixels. However, it is conventional in devices which utilize detectors of this type that data is compressed using various well known systems. Where this occurs, it is generally possible to convert the data back into the original format, although generally not without some loss of data or accuracy due to calculation errors.

For example, the output from a Bayer filter is frequently interpolated first to an "RGB" format, to provide the closest representation of the actual colour emanating from a particular point, as is well known in the art. This process may take various precise forms (including nearest neighbour, linear, cubic, cubic spline), but all generally require an assessment to be made about the two missing colours at points corresponding to each photosensor or sub-pixel, by examining the signals being received by certain surrounding photosensors.

This data may then be compressed for example into what is known as the YUV form in which "Y" represents luminance (Y), and U and V chrominance.

For the purposes of the present invention, where the generation of single or limited spectrum images is required, this process is not helpful. However, data compressed into YUV format may be converted back to an RGB form, which can be more readily used using a method known as matrix multiplication. Generally, the signals may be converted in accordance with the following formulae:

$$R=1.164(Y-16)+2.018(V-128)$$

$$G=1.164(Y-16)-0.813(U-128)-0.391(V-128)$$

$$B=1.164(Y-16)+1.596(U-128)$$

Therefore, it is possible to use detectors which are set up to process data directly into the YUV form. In this case however, selection of the required photosensor outputs will require the additional step of converting this data back, using formulae of this type.

Colour filter systems other than the Bayer system described above are also available and any of these can be used in the method of the invention. The selection of the filter system used will depend upon the availability of the appropriate chips or devices, but where a particular signal type, for example from a particular dye or fluorophore is being monitored, it may be possible to select a filter arrangement which would provide the greatest sensitivity in the waveband range in which the particular dye or fluorophore emits at greatest intensity. Thus for example, the Bayer filter system may be best suited to the detection of many of the commonly used green dyes, such as SYBR Green I or SYBR Gold.

Alternative filter systems may include red, green and blue (RGB) filters in different arrangements such as diagonal arrangement or octagonal arrangement (such as the Super-CCD developed by FujiFilm), as well as the RGBE sensor, which includes an emerald filter, as well as red, green and blue filters, and the complementary or CYGM sensor which includes equal numbers of cyan, yellow, green and magenta filters.

Foveon sensors, which comprise a 3-dimensional array of silicon photosensors may also be utilized in the method described above. The three dimensional array is possible because silicon absorbs light at different wavelengths at different depths. Therefore, by stacking photosensors tuned to absorb light in certain wavelength bands in the order of blue on top, green in the middle and red at the bottom, a full colour spectrum at each photosensor or sub-pixel point can be achieved.

For the purposes of the present method, it is necessary to select from amongst the layers of photosensors, those layers which are required to contribute to the target spectrum. For example, in order to detect signals in the red region, one would need to select output from the lowest layer of photosensors only.

The array may be sufficiently large to be able to form a 2-dimensional image of the reaction vessel, using light directly emanating from the vessel. However, if this is not the case, then a suitable focusing arrangement such as a conventional lens may be used to ensure that the entire surface of the reaction vessel is detected, or one or more fibre optic cables used to convey light from the reaction vessel to the detector.

In a particular embodiment, the detector is arranged to receive signals from a number of reaction vessels substantially simultaneously. Again, the array may be sufficiently large to be able to form an image of a number of reaction vessels, which are suitably spaced from one another. This may be achieved for example using a high density PCR array e.g. the BioTrove OpenArray platform.

However, if this is not possible, then a suitable focusing arrangement such as a conventional lens, or an arrangement of fibre optic connections to the detector, may be used to ensure that all reaction vessels are imaged.

Reaction vessels may, for example be arranged as a conventional multiwell plate such as a 48, 96 or 384 well plate.

In order to ensure that signals of various spectra are obtainable from each vessel, it is necessary that photosensors of each of the different colour filters are able to receive signal from each reaction vessel. However, the arrangement of the pattern of optical filters within most commercially available detectors with integrated optical filters are able to do this, even with relatively small reaction vessels, as the photosensors themselves are extremely small. Thus each individual reaction vessel will interact with a number of photosensors, and these should include some associated with filters of each of the colour set.

Where more than one reaction vessel is present, it is going to be necessary to be able to distinguish the output from individual reaction vessels. This may be done physically by locating the array of reaction vessels in a predetermined position relative to the detector, and then combining the signal received from those pixels which receive light from the specific reaction vessel, either directly or by way of a lens as described above, together for analysis.

Alternatively pattern recognition techniques may be used on the complete image produced by the detector to determine where specific reaction vessels are located before data analysis. This may make use of registration marks on the vessel or surround, e.g. using fluorescent ink or paint, or lights such as LED's.

Thus the use of a detector having an array of photosensors as described above allows for an entire two dimensional arrangement of vessels to have their emission acquired very nearly simultaneously, in each waveband, in particular without any moving parts or actuators.

Measurements of each waveband for each vessel can be made very nearly simultaneously, without the need for mechanical realignment, bringing multiple benefits. Since there is no need to wait for mechanical realignment, there is no interruption to the acquisition, and all wavebands are acquired concurrently. Although acquisition of the signals for all the wells can be achieved substantially simultaneously, it will be apparent that strict simultaneity will not be achieved because of the way in which the clock signal in the detector is used to switch each pixel "on" in sequence, and "off" in sequence, so that, although the clock rate is substantially faster than the scanning rate of the whole detector, there is, nevertheless, an element of sequentiality. However, for parallel exposures, with a 45 MHz pixel clock, there is effective simultaneity, at least to the levels required here, and therefore the acquisition will hereinafter be described as simultaneous, even though it will be appreciated that it is not absolutely simultaneous.

Furthermore, if required each waveband can be acquired nearly all the time, rather than the acquisition time for a waveband being reduced to the time for which the system is configured for that waveband. The temperature and other properties of the observed reaction will be nearly identical for the image acquired in each waveband, allowing for more precise removal of spectral crosstalk and other noise. Temperature and other corrections can be applied using a single set of parameters, leading to easier and more accurate analysis.

Depending on the other elements of the apparatus, there may be other benefits—for example the simultaneous acquisition of each waveband from the or each vessel means that in systems where there may be fluctuations in the excitation source, each waveband and vessel will be acquired at the same excitation level. Any physical changes in the vessel, such as vessel movement or bubble formation, condensation or movement of contents will affect each waveband acquisition equally. This is a considerable benefit in cases where levels of one) often passive) dye are used to normalise levels of another (often active) dye.

Since there is no need to alter the acquisition wavebands or vessel/detector alignment, for example by physical movement, the detector can acquire data with minimal interruption. Since the detector can acquire all available wavebands just as easily as any subset of wavebands, there is no need to work with a reduced waveband set, and this increases opportunities for later analysis. Physical alignment within the machine is also rendered less critical, since the detector only needs to be aligned to the vessels, rather than to external filters etc., and any minor misalignment can be corrected for by processing of the detector image, for example pattern recognition and/or registration marks as described above.

An additional benefit of the integration of the photosensors sensitive to each spectrum into the detector array is that the photosensors used for detection of each waveband are spread across the detector array, and are interleaved in such a way that for each photosensor detecting any given waveband, there are photosensors detecting each other wavelength either immediately adjacent or very close by (or in the case of Foveon detectors, at the same point in two dimensions). Hence spatial corrections to the images for each waveband can be applied similarly or identically, making analysis easier and also enabling better correction, for example for flat field correction for illumination intensity, properties of optical system, etc.

In order to generate a detectable signal from a chemical or biochemical reaction, for example using fluorescent signaling reagents, it is frequently necessary to illuminate the reaction mixture in order to provide light energy, for example for the fluorophore to absorb, so as to allow it to emit light at its characteristic spectrum. By utilizing the method described above, a single illumination source can be used to illuminate a plurality of reaction vessels.

Suitable illumination sources include u.v, Halogen, Xenon or fluorescent lamps, Light Emitting Diodes, Lasers, or some combination of these sources. This excitation causes fluorescent dyes or markers which are contained with the reaction vessel to emit light with a characteristic spectrum in the range of the spectrum suitable for the detector type, and this can then be picked up by the detectors.

Excitation sources are preferably short wavelength (ultraviolet) sources in order that the output falls substantially outside the sensitivity of the sensor, reducing need for filtering and allowing use of all detector channels without interference from reflected excitation.

However, if desired or necessary it may be advisable to place a filter between the illumination source and the detector, which is arranged to prevent or reduce the amount of incident light reaching the detector from the illumination source itself. For example, where the excitation source is a u.v. lamp, a u.v filter or dichroic mirror, or other optical devices, may be provided between the lamp and the detector to prevent u.v. light reaching the detector and interfering with its operation. In particular also, the method is suitably carried out in a darkened or dark room, so as to minimize interference from ambient light.

The integrated detector has clear advantages in applications using multiple sources or configurations of excitation, such as excitation sources with multiple filters or different switchable emitters. When such systems are used with detectors having moving parts, the time required for movement or switching of both the emission and detection systems to achieve each combination of excitation and detection waveband or vessel alignment can become prohibitive, leading to difficult choices of which combinations to use. For example, with 3 emission settings and 3 detection waveband settings, there are 9 possible combinations, all of which could potentially be useful, but this in turn requires 9 interruptions to acquisition, which for many applications will take a prohibitively long time.

Using a detector in accordance with the method described herein, the number of interruptions is reduced to 3, with all combinations being acquired, and less moving parts required.

Using detectors as described above may allow for the capture of an image at a single point in time. However, it is also possible, where the detector is for example, part of a video recording system, to monitor the signals repeatedly, or even substantially continuously over a period of time.

Changes in intensity of for example a signal in a particular waveband over a period of time may be indicative of the progress of a chemical or biochemical reaction, and the precise nature of those changes may be effectively monitored substantially continuously using the method described herein.

By appropriate manipulation of controls of the detector, data may be acquired at one or more points which are precisely timed in relation to an interval of excitation, thus yielding data on the change in fluorescence with time. Thus the method can be used in the context of Time Resolved fluorimetry (TR fluorimetry). Suitable manipulation of the controls of the detector would be readily determined by a skilled person, and thus this provides an extremely cost effective way to do TR fluorimetry.

This may be particular useful, as mentioned above, in relation to a polymerase chain reaction (PCR) which conducted in the presence of at least one signaling fluorophore. As is known in the art, particular examples of fluorophores which may be included in a PCR reaction without interfering with the progress of the reaction include intercalating dyes or fluorescently labeled probes or primers, or combinations of these. The precise format of the fluorescent assay is immaterial to the operation of the invention, since by appropriately selecting signaling moieties or fluorophores, a number of different signals may be monitored.

The signals may be monitored continuously or taken as certain particular time points during each thermal cycle only, so that the changes over cycle number can be seen.

One simple form of monitoring of a PCR reaction is described in EP-A-512334, and used a DNA binding agent which emits a signal when it is bound to double stranded DNA molecule which is distinguishable, in particular in intensity, from that when it is free in solution. As mentioned above, this system allows the increase in DNA in the mixture during the PCR to be monitored, and this provides information as to whether the reaction is occurring, and even, how much target material was present in the starting sample.

Using the method of the invention, the signals characteristic of the major emitting wavebands of the specific DNA binding agent used are selected. By analyzing the images produced in this way, increases in intensity characteristic of an increase in the amount of DNA present in the system can be detected.

In other systems, the signaling agent is a fluorophore such as a fluorescent label which is attached to an oligonucleotide probe which specifically hybridizes to a target nucleic acid sequence of the PCR.

In the TAQMAN™ case, a dual labeled probe is used. Thus the oligonucleotide probe contains a second fluorophore, which is able to exchange fluorescent energy with said fluorescent label when present together on the probe. By utilizing in the reaction a polymerase having 5'-3'exonuclease activity, this probe is digested during an extension phase of the reaction, thus changing the interaction of the labels and giving rise to a signal.

In a variation on this method, a first and a second oligonucleotide probe is used. The second probe carries a second fluorophore, which is able to exchange fluorescent energy with said fluorescent label on the first oligonucleotide probe. The probes are designed to hybridize to the target nucleic acid of the PCR at locations which are sufficiently close to allow the respective probes to exchange energy and therefore, the signal is modified.

Provided suitable combinations of dyes are utilized, the method of the invention can be used to monitor any of these assays. Particular fluorophores or combinations of fluorophores would be well known to the skilled person, but they include moieties such as fluorescein, FAM, JOE, SYBR Green I, ethidium bromide, cyanine dyes such as Cy5 and rhodamine dyes.

The method may also be used to carry out for example melting point analysis, for example using a DNA binding agent as described above. If a reaction mixture containing a nucleic acid is heated in the presence of an intercalating dye, and the signal from the dye monitored over time, the point at which the signal of the DNA binding agent changes is indicative of the temperature at which the denaturation occurs.

According to a further aspect, the invention provides apparatus for use in a method as described above, said apparatus comprising a detector comprising a plurality of photosensors, arranged in an array, photosensors within the array being arranged to receive light within a specific waveband range only, and a controller arranged to receive and combine signals from photosensors sensitive to one or more of the said waveband ranges and to relate the output from a subset of photosensors which receive light of the same waveband range, and/or the relationship between the outputs of more than one subset to determine the signal having the specific spectrum emitted from a reaction vessel.

Apparatus of this type will include further features as necessary or desirable to conduct specific or particular embodiments of the method.

For example, it may further comprise filter wheels or diffraction gratings to separate the signal falling on individual photosensors into specific waveband ranges. However, in a particular embodiment, the detector will be provided with set of differently coloured optical filters in fixed relationship to the array of photosensors and arranged to ensure that individual photosensors or groups of photosensors within the array are activated by light within a specific waveband range only, wherein the differently coloured optical filters being arranged in a pattern, such that adjacent photosensors or groups of photosensors receive light of different waveband ranges. The pattern may be a 2-dimensional array such as the Bayer or other RGB systems, or the complementary CYGM of RGBE systems, or 3-dimensional as in the Foveon system. In particular however, the differently coloured filters comprise red, blue and green colour filters, and these are suitably arranged in a Bayer pattern.

Conveniently, a single filter sheet carries all filters of one or more colours, arranged in an appropriate pattern, so that by superimposing a sheet containing each colour type, a complete mask is created. Alternatively a single sheet may have filters of more than one, and suitably all required colours in a suitable arrangement, for example a Bayer mask arrangement.

The detector may be any of the available detectors which comprise an array of photosensors including CCD, photodiode, PMT and CMOS detectors. In particular the detector is a CCD or CMOS detector, for instance a CCD.

The apparatus may further comprise a support for positioning said detector in fixed relationship to a reaction vessel, so that the output from the reaction vessel can be detected. This may take the form of a clamp or the provision of an integrated holder for a reaction vessel which is in fixed relation to the detector.

In a particular embodiment, any apparatus holder is suitable for holding a plurality of individual reaction vessels, which may be included in a multi-well plate, such as a 48, 96 or 384 well plate as described above.

If necessary, the apparatus may further comprise a lens, which is arranged to focus light emanating from the reaction vessel or vessels onto the detector. Additionally, a fresnel lens above the vessels may improve performance by giving closer to parallel paths for excitation and/or reading of each vessel.

It may further comprise an illumination source, arranged to illuminate the one or more reaction vessels when these are in a position so as to be detectable by the detector. Suitable illumination sources include u.v, Halogen, Xenon or fluorescent lamps, Light Emitting Diodes, Lasers, or some combination of these sources, as discussed above, but in particular may be an ultraviolet lamp.

If required, a filter, for example an ultraviolet filter, may be positioned between the illumination source and the detector so as to reduce interference in the signal.

Where the apparatus is specifically intended to monitor reactions which involve thermal cycling such as PCR, a thermal cycler, such as a block heater arrangement able to hold a multi-well plate, may be provided as part of the apparatus.

If necessary, a cooling or refrigeration device may be provided for cooling the detector in particular where this is a CCD, to increase signal to noise ratio and achieve more accurate readings.

Apparatus of this type, where the controller is arranged to monitor one or more reactions continuously, thus constitutes a real-time PCR instrument.

In a further aspect, the invention provides a method for detecting a signal of a specific spectrum emitted in the course of a chemical or biochemical reaction, said method comprising monitoring the reaction using a camera chip having an integrated colour filter, and determining the signal on the basis of the individual colour channel output. Particular embodiments of this method are similar to those described above. In particular the specific spectrum is characteristic of a particular reagent. Furthermore, using this method, more than one specific spectra can be determined, provided that these are different in nature.

The invention will now be particularly described by way of example with reference to the accompanying diagrammatic drawings in which:

FIG. 2 illustrates a Bayer filter arrangement where "R" stands for red, "G" for green and "B" for blue filters;

Figure 1:
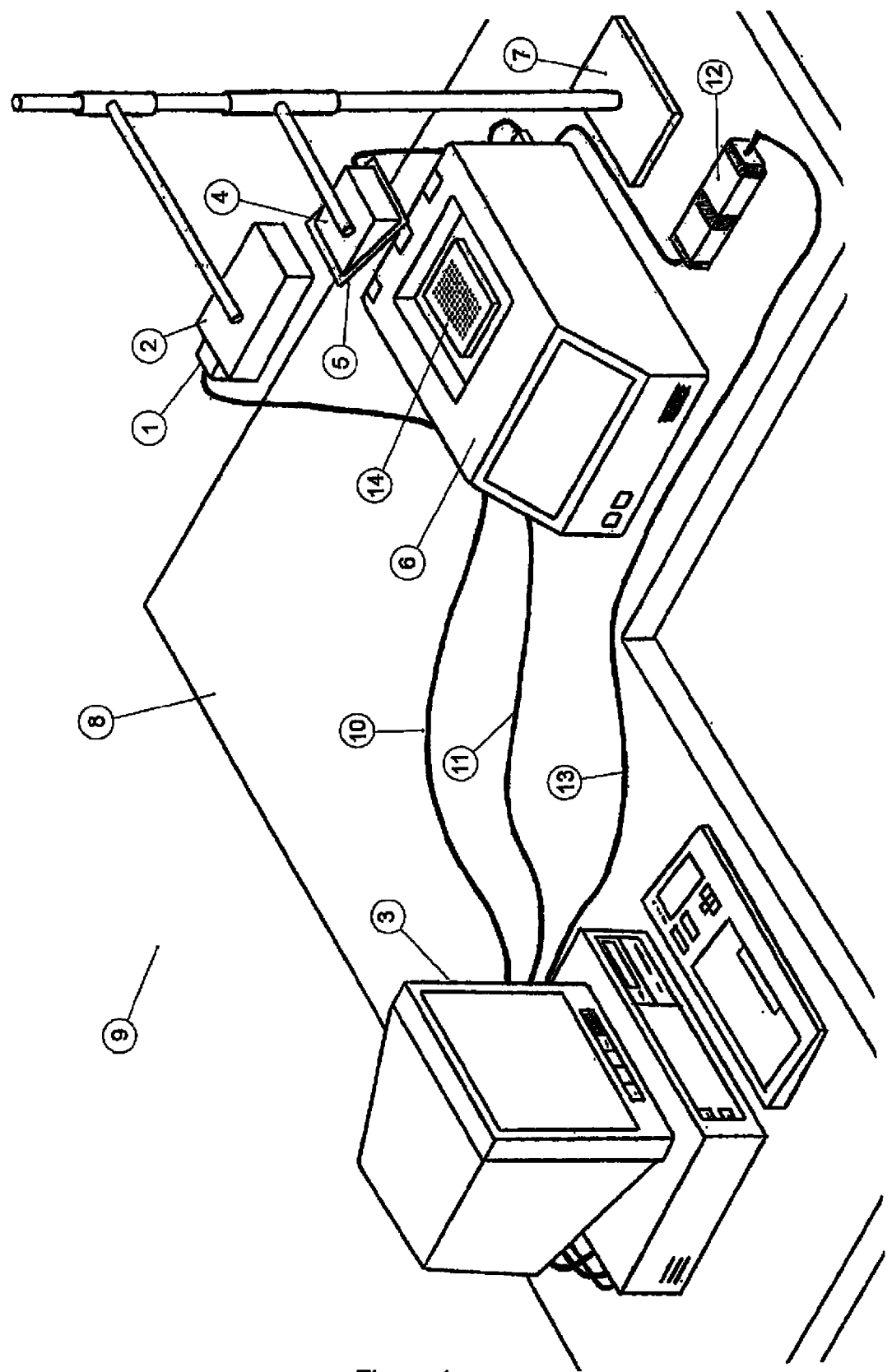
FIG. 1 is a schematic representation of apparatus for monitoring PCR reactions being conducted in a multi-well plate.

The apparatus shown in FIG. 1 is suitably arranged in a dark-room or other light-proof enclosure to eliminate unwanted illumination. Individual components are suitably mounted or placed on a stable bench (8).

The apparatus itself comprises a detector (1) in the form of a CCD chip with an integrated filter. A particular example of such as chip is the Sony ICX098BQ with integrated filter. This is a diagonal 4.5 mm (Type ¼) interline CCD solid-state image sensor with a square pixel array which supports VGA format.

Progressive scan of the chip allows a readout of the individual levels of each pixel of the detector, within approximately 1/30 second. This chip features an electronic shutter with variable charge-storage time which makes it possible to realize full-frame still image without a mechanical shutter. High resolution and high color reproducibility are achieved through the use of R, G, B primary color mosaic filters, in a Bayer filter pattern.

Further, high sensitivity and low dark current are achieved through the adoption of HAD (Hole-Accumulation Diode) sensors.

The driver and Universal Serial Bus (USB) interface electronics for this chip are provided by a suitable host camera apparatus such as a webcam (2), and in particular, a Philips Toucam II Pro (PVC840K) webcam modified by removal of the case and other non-essential parts and rehoused in a new enclosure.

The detector (1) is positioned above an array of reaction vessels (14), each of which contains a reaction mixture, suitable for conducting a PCR and including a fluorophore as a label. A UV lamp (4) is positioned alongside the array, with these components being held in place by a mounting system (7). The UV lamp (4) is suitably one which gives strong stable emission over a narrow spectrum such as a Phillips lamp and is able to provide excitation for the fluorophores (e.g. ethidium Bromide) in the PCRs, thereby to cause light to be emitted at wavelengths detectable by the detector (1).

A UV-pass filter (5) is placed over the lamp (4). This plays no role in distinguishing the different wavelengths of emitted light, and is fixed in place, but serves to block any visible light originating from the UV lamp from reaching the vessels or detector, whilst allowing UV light to excite the fluorophores in the PCRs. This increases the signal to noise ratio of detected visible light.

A thermal cycler (6) (a Techne Touchgene) is used to control the temperature of the array of reaction vessels (4) to allow PCRs to progress.

A Personal Computer (3) (see later for details) is connected to the detector (1) by a USB link (10), to the thermal cycler (6) by a serial communications link (11) and also to the lamp (4) by a lamp control (13). As a result, the PC (3) is able to control all the components of the apparatus, to ensure that the PCR progresses and to acquire images of the reaction vessels (14) from the detector (1).

More particularly, control of the lamp (4) is effected as follows.

The UV lamp (4) is powered via a ballast control (12), which provides for rapid modulation of the UV light emitted by the lamp by control of a lamp switching unit which switches the provision of power to the ballast from the electrical connections. The lamp switch is controlled by an output pin of the PC parallel port connected via cable (13), so that setting this parallel port output high or low will switch the lamp switch on or off, and thus enable or disable UV illumination, respectively.

As already stated, the detector (1) is connected to the Personal Computer via the USB interface (10). The PC runs a customised real-time capable Linux Kernel, having the Philips Webcam (PWC) video capture driver installed. Acquisition software running on the PC acquires images from the detector via the Video4Linux2 (V4L2) Application Programming Interface (API).

Preferably the detector (1) is configured to yield raw output images, having the unprocessed acquisition values for the photosensors of the CCD sensor. Where the Philips Webcam PVC840K has been configured in this way, it should be run in colour mode 15, which is YUV4:2:0P. This is "raw" mode, and gives an image where the 640×480 Y channel (first channel) actually contains the direct values of the red-, green- and blue-filtered photosensors of the camera, arranged in 2×2 blocks in the form of a Bayer mask as illustrated in FIG. 2. This mode allows for higher signal to noise ratio and sensitivity, by avoiding the degradation and data loss associated with conversion of the subpixels into a YUV colour space.

Data in this format is then processed by averaging the two green subpixels in each block, to yield a 320×240 RGB format image, preferably using a precise representation for each colour channel, such as floating point representation rather than the more usual 8 bit representation. This has the useful effect of giving a greater precision in the green value per pixel, which is useful for common green dyes.

Alternatively data in this raw format may be left unaltered to give a slightly higher spatial resolution in the green channel. In practice, the conversion to a 320×240 RGB image has been found to be easier to use in later analysis stages, and this image format is used in the embodiment described.

In the event that the detector (1) (PVC840K) is not configured to produce raw output images, the YUV4:2:0P mode will provide images in YUV format. These each consist of a 640× 480 array of Y values, and 320×240 arrays of U and V values. These may be processed by averaging each 2×2 block of Y values, to give a higher precision 320×320 Y array. This can then be converted by standard techniques (e.g. matrix conversion), taking each YUV pixel to the equivalent RGB pixel. This will yield a 320×240 RGB format image, which may then be processed in the same way as an image produced via raw detector output as described above.

The applicants have found that although the conversion from actual CCD subpixels to YUV colour space, and back again, degrades the signal, this is not enough to prevent utility. Some degradation also results from the demosaicing process used, which may average neighbouring subpixels.

EXAMPLE 1

Figure 3:
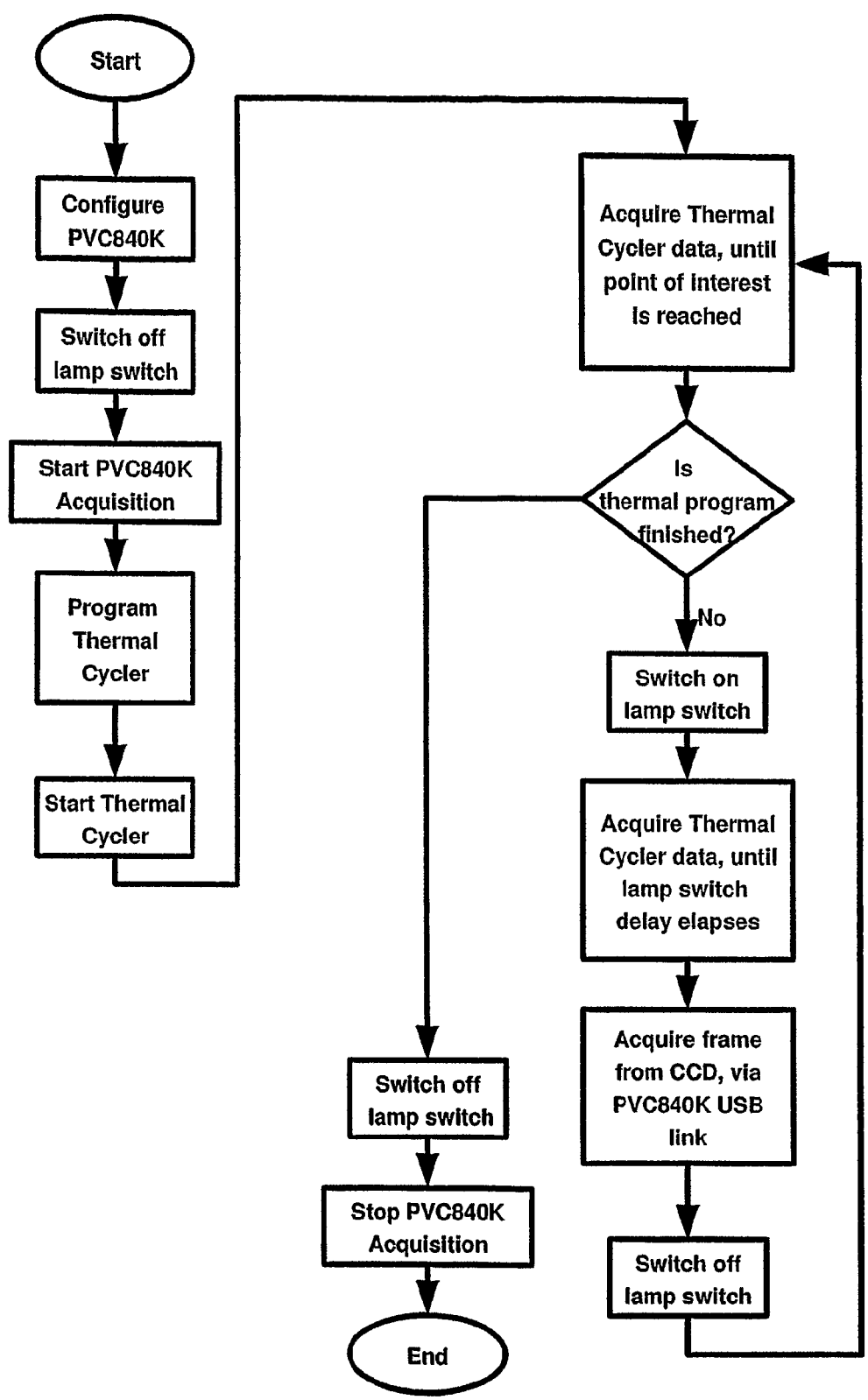
FIG. 3 is a flow chart illustrating the operations carried out in order to use the apparatus of FIG. 1 for monitoring a chemical or biochemical reaction such as a PCR using a thermal cycler.

An experiment was performed using the apparatus described above by running a software program on the PC, which performs the steps illustrated in FIG. 3.

Configuration of the PVC840K.

Configuration of gain and exposure was chosen to yield good amplification of low signal levels, at a high resulting signal to noise ratio, and without saturating the detector. For this purpose, values of about 0.8 of full scale for each setting were found to be adequate. In addition, settings for brightness, contrast and gamma are chosen to give a substantially linear relationship between the actual measured CCD subpixel levels, and the levels reported by the PVC840K via USB connection, to give best fidelity to the actual light levels. Use of mid-range values for both brightness and contrast, and minimum value for gamma gives good results. Finally, automatic gain control (AGC) and white/red/blue balance are disabled, to prevent variation in fluorescence being masked by compensation by the PVC840K.

Initialisation of Acquisition by the PVC840K.

Once this has been set, the PVC840K will acquire frames at the configured frame rate, which was generally set to 5 frames per second to give a good compromise between time resolution and sensitivity.

Programming and Initialisation of a Thermal Program on the Thermal Cycler, Via Serial Communication.

Monitoring of the progress of the thermal program on the thermal cycler, was effected using serial communication. When the thermal cycling was at a point of interest (generally a particular temperature stage of each cycle, or a temperature ramp performed for melt analysis), the UV lamp switch was switched on, and after a configurable delay, each image acquired from the PVC840K was collected and stored for later analysis (or for analysis during the run, as appropriate). When the point of interest had passed, the UV lamp switch was switched off again.

Figure 4:
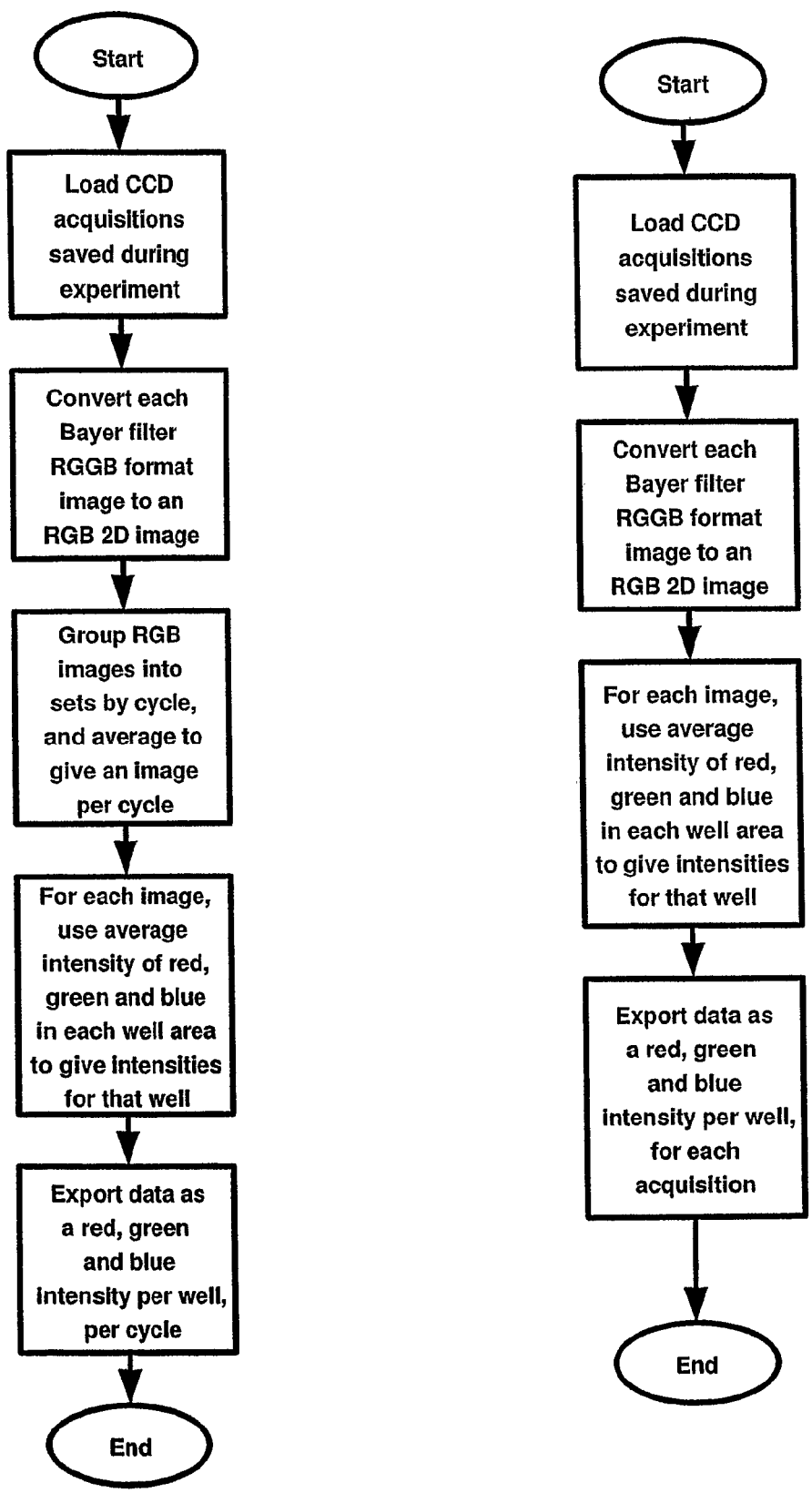
FIG. 4 is a flow chart illustrating the operations which are carried out during the analysis of the results obtained using the apparatus.

When the thermal program was complete (as signaled by the Techne instrument) the PVC840K acquisition was stopped, and the program proceeded to analyse the data, using the stages illustrated in the flow chart of FIG. 4A.

Data analysis was performed using the ImageJ image manipulation software, with the stored acquired images in raw or YUV format being loaded into the software via an import plugin, produced by the applicants, which follows the process described above to convert the raw or YUV format images into an RGB format for further processing. This processing consisted of combining each image taken during each cycle into a single image. This set of cycle images may then be converted to well intensities by use of circular regions which yield an average intensity in each channel, per well.

This data could then be easily exported for further analysis, for example in Excel. This process yielded the conventional amplification curves, characteristic of "real time' PCR data analysis.

The apparatus was also used for melt data analysis, and the operation was broadly similar, but each acquired frame was processed as for a cycle, and well intensities are then exported against temperature as reported by the thermal cycler (see FIG. 4B).

The data could be further processed by deconvolution of dye levels. This took account of the spread of dye emission across more than one colour channel of the CCD, and can be achieved by use of a matrix deconvolution method. The matrix used for deconvolution is derived from measured spectra of known quantities of each dye of interest, which may additionally be derived at multiple temperatures, with the matrix used for deconvolution of a given frame being produced by interpolation of the known matrices at the nearest temperatures.

An example of the use of the system for deconvolution of data to distinguish two dyes with similar emission spectra will now described. The following data and calculations illustrate the process and feasibility of distinguishing two dyes with similar emission spectra, which are mixed in a reaction vessel at different concentrations and ratios. Each vessel emits light which is then detected by multiple sensor elements, including at least one element sensitive to each of three sub-spectra. These sub-spectra will be termed red, green and blue, since they correspond roughly to red, green and blue coloured light.

The two dyes used are FAM and VIC, two dyes commonly used in chemical or biochemical reactions, where both dyes are visually predominantly green in colour, but where FAM has a blue or aqua tint, and VIC is closer to a yellow or orange tint. The ability of a sensor array as described above to distinguish between these two dyes illustrates the usefulness of the system.

Figure 5:
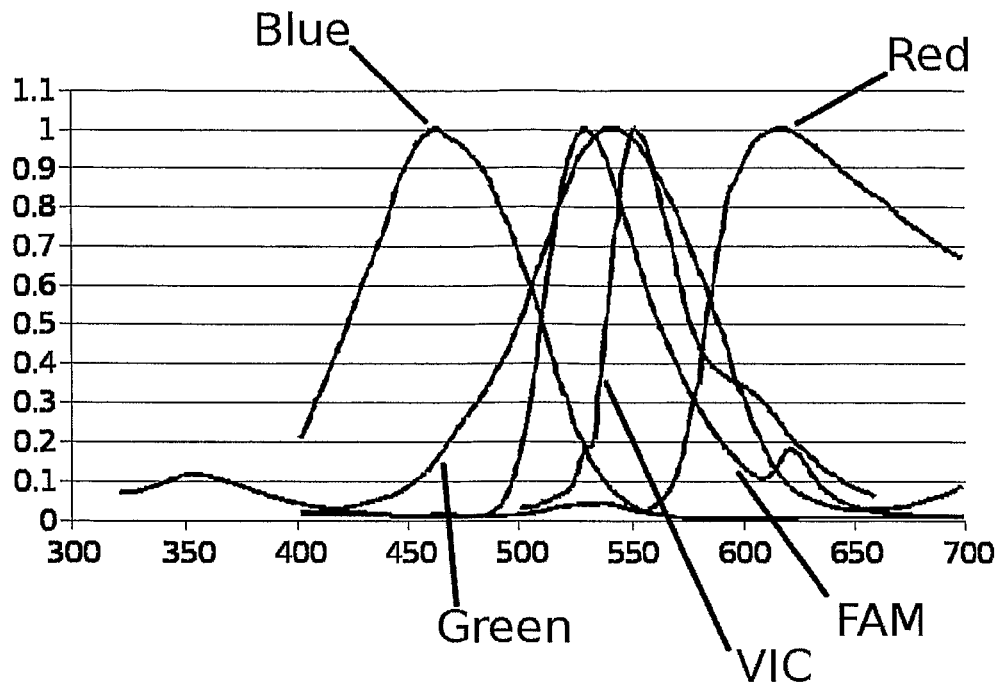
FIG. 5 is a graph showing the measured and normalised response spectra of red, green and blue sensors, as well as the measured and normalised emission spectra of FAM and VIC dyes.

The graph illustrated in FIG. 5 shows the measured and normalised response spectra of the red, green and blue sensors—this shows the variation of the relative degree of output response with input light wavelength. In addition, the measured and normalised emission spectra of the FAM and VIC dyes are plotted, showing the variation of the relative intensity of emitted light with wavelength.

Note that the response and emission spectra have been normalised. In the case of the response spectra, this can be easily allowed for when interpreting measured data, by scaling the output in each sub-spectrum to duplicate this normalisation, before analysis. In the case of the dyes, all further calculations are carried out in units of the concentration of dye required to produce the normalised emission spectrum seen—these units can be readily measured and used to convert the results back into dye concentration, dilution, or whatever other measure is useful for the application.

Figure 6:
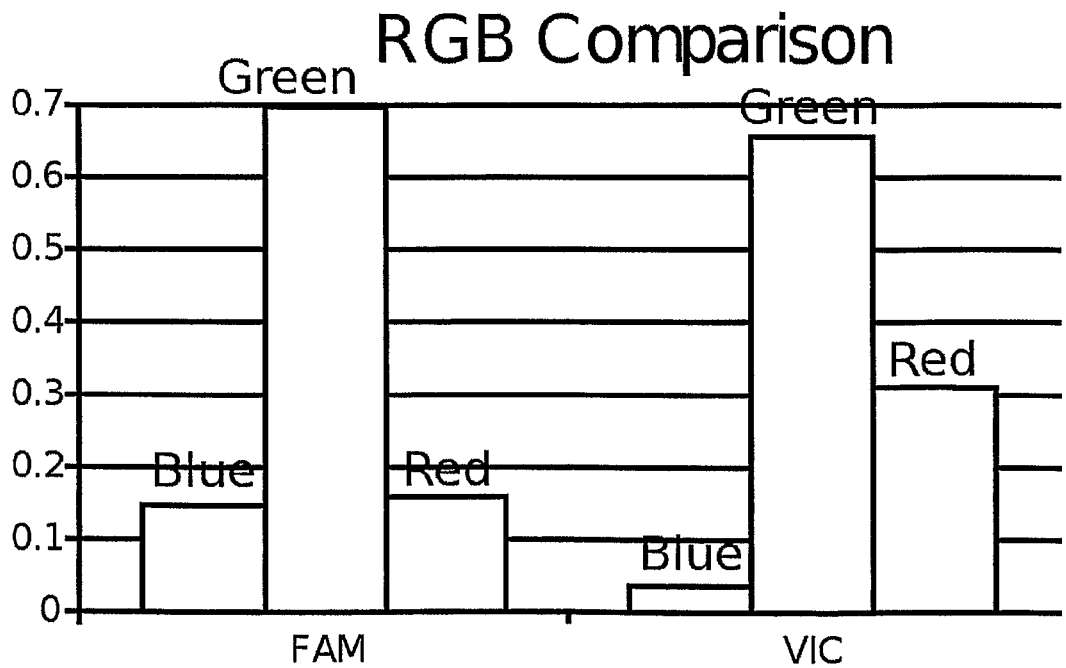
FIG. 6 is graph showing the calculated response of sensor channels to FAM and VIC.

The graph illustrated in FIG. 6 shows the calculated response of the sensor channels to FAM and VIC. For each sub-spectrum, the integral is found of the pointwise product of the sensor channel response curve and the emission curve of the dye in question. This yields an RGB spectrum for each dye. As can be seen, FAM shows a stronger blue response, and VIC a stronger red response. This is a simplification—since the RGB spectrum is used in a full deconvolution method, each channel is used, and differences in each channel are taken advantage of to provide for accurate discrimination of the dyes.

To test the deconvolution method, a series of RGB observations are prepared, consisting of a quantity of FAM, VIC, and a degree of random noise, with an amplitude given relative to the average green intensity of FAM and VIC (e.g. 5% of FAM.VIC average green intensity). The RGB observations are then deconvoluted, by providing the expected RGB spectra of both dyes, and the observed RGB spectrum to the deconvolution method, which produces an observed intensity for each dye. The results for an initial test to deconvolute each combination of a n*10% FAM and m*10% VIC, for n, m from 0 to 10, with an additional 5% random noise, are given in the attached spreadsheet (giving a matrix of 11×11). Each is tested using an 8×8 array of readings to represent a minimal well area imaged using an array sensor such as a CMOS sensor. When the results are averaged across the well area, the errors on FAM and VIC concentration are less than the noise level, <approx 2%. An impression of the accuracy of the method is given by observing the accuracy of the calculated VIC levels, in the presence of varying levels of FAM (which are themselves distinguished with similar accuracy), as shown in FIG. 7.

Figures 7, 8:
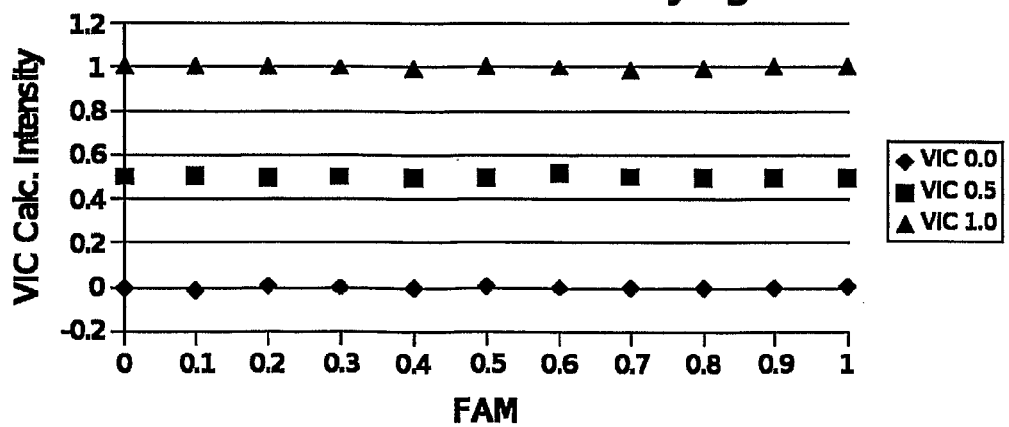
FIG. 7 is chart showing calculated VIC levels in the presence of varying levels of FAM.
FIG. 8 is graph showing the results of FIG. 7.

These results are shown graphically in FIG. 8—the ideal result would be a straight line for each data set, indicating that the admixture of FAM dye has no effect on the calculated VIC concentration, in turn indicating that the sensor and deconvolution system are capable of independently resolving the two dye concentrations. As previously stated, these calculations yield a maximum error of 2.063%, which is less than the added noise (accuracy can be lower than noise level due to the beneficial effect of the averaging of multiple sensor readings per vessel).

The deconvolution method is a matrix method which decomposes a vector given by a reading, which is a set of values for the response of the sensor in each subspectrum, into a vector in terms of levels of each of a set of expected dyes, which is directly useful in interpreting the experiment. For example, in the system described above, readings are made in the red, green and blue subspectra. Hence a reading (denoted O for observed) is in general:

$$O = \begin{bmatrix} r \\ g \\ b \end{bmatrix}$$

r, g and b are the scalar responses in the corresponding channels. However we are directly interested in the levels of two dyes, rather than the red, green and blue responses. Therefore we wish to calculate a vector of dye levels:

$$C = \begin{bmatrix} d_1 \\ d_2 \end{bmatrix} = \begin{bmatrix} f \\ v \end{bmatrix}$$

where C is the calculated dye vector, f is the relative FAM concentration (dye 1, $d_1$), and v is the relative VIC concentration (dye 2, $d_2$). The starting point for the analysis is the selection of dyes of interest in the vessels. In this case, we expect FAM and VIC dyes to be present in the reaction, and request concentrations of these two dyes to be calculated. For each dye, the expected response in each detector channel is calculated—this is done by finding the integral of the pointwise product of the channel response subspectrum and the emission curve of the dye in question. This yields an RGB spectrum for each dye—as shown in the graph of FIG. 6. As discussed above, FAM and VIC both give a strong response in the green sub-spectrum, but their responses differ in the red and blue subspectra:

$$D_1 = F = \begin{bmatrix} 0.15 \\ 0.7 \\ 0.16 \end{bmatrix}$$

$$D_2 = V = \begin{bmatrix} 0.03 \\ 0.66 \\ 0.31 \end{bmatrix}$$

Here we label F as dye matrix 1, $D_1$ and V as dye matrix 2, $D_2$. An additional component is added, to model the noise component of a signal, which is expected to be of equal size in each sub-spectrum (where noise is present at different levels in each sub-spectrum, this can of course be modelled using the expected levels in place of the value of 1 used here for each sub-spectrum):

$$D_3 = N = \begin{bmatrix} 1 \\ 1 \\ 1 \end{bmatrix}$$

Noise is here termed $D_3$ since it is treated as a component of the signal, identically to a dye. Now, since we consider the observed rgb-space reading O to be a sum of dyes, we see that it must be the sum of the concentrations of the dyes, multiplied by their individual spectra:

$$O = \Sigma d_i D_i$$

We wish to find C by finding its components, $d_i$.
Consider:

$$O \cdot D_j = (\Sigma d_i D_i) \cdot D_j = \Sigma d_i (D_i \cdot D_j)$$

By taking the dot product of the observed spectrum with each dye in turn, we produce a matrix S:

$$S = \begin{bmatrix} O \cdot D_1 \\ O \cdot D_2 \\ \vdots \end{bmatrix} = \begin{bmatrix} D_1 \cdot D_1 & D_2 \cdot D_1 & \ldots \\ D_1 \cdot D_2 & D_2 \cdot D_2 & \ldots \\ \vdots & \vdots & \ddots \end{bmatrix} \begin{bmatrix} d_0 \\ d_1 \\ \vdots \end{bmatrix} = PC$$

where it can be seen that the matrix multiplication gives the same sum on each row as shown in the formula above. The Matrix P is constructed by making each element equal to the dot product of the dye spectra corresponding to the row and column indices, hence it is easy to calculate from the known dye spectra.

It is now only necessary to take the matrix S, calculated from the observed spectrum and known dye spectra, and premultiply by the inverse of the dye matrix P:

$$C = P^{-1} S$$

Hence yielding the desired vector C, which shows the concentration of each dye. It can be seen from the method that it is possible to distinguish a number of dyes equal to the number of subspectra measured, and that where there are less dyes than subspectra, it is additionally possible to directly separate the effects of background noise from dye levels. The method described was implemented in the Java programming language, and used to produce the data described. Although, the data is for deconvolution of a pair of dyes and noise, the calculations necessary to deconvolute three dyes are similar.

The invention claimed is:

1. A method for determining a level of a particular characteristic specific spectrum representing a particular characteristic of a chemical or biochemical reaction, from light which is emanating from at least one reaction vessel of a plurality of reaction vessels in the course of the reaction, the light having a general spectrum comprising a number of different specific spectra including the particular characteristic specific spectrum, at least two of the different specific spectra at least partially overlapping, the method comprising:
   conducting the reaction in the at least one reaction vessel, which is arranged so that the light having the general spectrum emanates from the reaction vessel and a received portion of the light is received by a detector comprising a plurality of photodetectors of different types distributed throughout a two-dimensional array of photodetectors, each photodetector of a particular type comprising a photosensor and a particular type of filter that passes light of a particular waveband range, wherein at least two different particular waveband ranges at least partially overlap, and wherein a subset is formed by some or all photodetectors of the same type;
   monitoring output from a plurality of subsets of at least two of the different types of photodetectors; and
   utilising the outputs from the plurality of subsets to deconvolve the general spectrum of the received portion of the light based on known spectra that could emanate from the at least one reaction vessel during the reaction, so as to differentiate between the different specific spectra and thereby determine a light level of the particular characteristic specific spectrum;
   wherein the received portion of the light is monitored repeatedly over a period of time.

2. A method according to claim 1 wherein the particular characteristic specific spectrum is characteristic of a particular reagent or state of a particular reagent within the reaction vessel, or is derived from a single species of fluorophore, present in the reaction.

3. A method according to claim 1 wherein the different types of photodetectors comprise filters of corresponding different types, and the different types of filters comprise at least red, blue and green colour filters, which are arranged in a Bayer pattern.

4. A method according to claim 1 wherein the chemical or biochemical reaction is a polymerase chain reaction (PCR) conducted in the presence of at least one fluorophore chosen from the group consisting of:
   fluorophores which intercalate with nucleic acid;
   fluorophores which are modified by the PCR process; and
   fluorophores which provide for fluorescent energy transfer between them.

5. A method according to claim 4 wherein the fluorophore is a fluorescent label attached to a first oligonucleotide probe which specifically hybridizes to a target nucleic acid sequence of the PCR and wherein the first oligonucleotide probe contains a second fluorophore, which is able to exchange fluorescent energy with the fluorescent label when present together on the probe, wherein a polymerase having 5'-3' exonuclease activity is utilized in the PCR so as to digest any first probe bound to target nucleic acid during an extension phase of the reaction.

6. A method according to claim 1 wherein the detector is arranged to receive signals from the plurality of reaction vessels simultaneously.

7. A method according to claim 1 wherein the known spectra are determined from calibration reactions emanating light signals having known spectra.

8. A method for determining a level of a particular characteristic specific spectrum representing a particular characteristic of a chemical or biochemical reaction from light which is emitted in the course of the reaction and has a general spectrum comprising a number of different specific spectra including the particular characteristic specific spectrum, at least two of the different specific spectra overlapping, the method comprising:
   receiving a received portion of the light from the reaction;
   monitoring the received portion of the light using a camera chip having a plurality of integrated colour filters to produce a plurality of different colour channel outputs, wherein different colour filters pass light of different particular waveband ranges, wherein at least two different particular waveband ranges at least partially overlap; and
   deconvolving the general spectrum of the received portion of the light using a processing system based on known spectra that could emanate from the reaction vessel during the reaction so as to differentiate between the different specific spectra and thereby determine a light level of the particular characteristic specific spectrum on the basis of the different colour channel outputs of the camera chip;
   wherein the received portion of the light is monitored repeatedly over a period of time.

9. A method according to claim 8 wherein the particular characteristic specific spectrum is characteristic of a particular reagent, and wherein the level of more than one different particular characteristic specific spectrum is determined.

10. A method according to claim 8 wherein the known spectra are determined from calibration reactions emanating light signals having known spectra.

* * * * *